US00PP22792P3

(12) United States Plant Patent
Danziger

(10) Patent No.: US PP22,792 P3
(45) Date of Patent: Jun. 12, 2012

(54) ***SANVITALIA* PLANT NAMED 'DANVITAL4'**

(50) Latin Name: *Sanvitalia speciosa*
Varietal Denomination: DANVITAL4

(75) Inventor: Gavriel Danziger, Moshav Nir-Zvi (IL)

(73) Assignee: Danziger 'Dan' Flower Farm

( * ) Notice: Subject to any disclaimer, the term of this patent is extended or adjusted under 35 U.S.C. 154(b) by 0 days.

(21) Appl. No.: 12/805,427

(22) Filed: Jul. 30, 2010

(65) Prior Publication Data

US 2012/0030849 P1 Feb. 2, 2012

(51) Int. Cl.
*A01H 5/00* (2006.01)

(52) U.S. Cl. ..... Plt./476

(58) Field of Classification Search ..... Plt./476
See application file for complete search history.

(56) References Cited

OTHER PUBLICATIONS

Printout of application information from Community Plant Variety Office (CPVO) website for corresponding CPVO application No. 2010-1301 filed Jul. 2, 2010 (1 page) (http://www.cpvoextranet.cpvo.europa.eu).

*Primary Examiner* — June Hwu

(57) ABSTRACT

A new distinct cultivar of *Sanvitalia speciosa* plant named 'DANVITAL4', characterized by its mounding and trailing plant habit; compact growth habit with good branching; about 200 inflorescences per plant, consisting of ray florets that are primarily yellow in color and disc florets that are primarily green in color; and medium tolerance to heat.

2 Drawing Sheets

Latin name of the genus and species of the claimed plant: *Sanvitalia speciosa.*

Variety denomination: 'DANVITAL4'.

BACKGROUND OF THE INVENTION

The present invention relates to a new and distinct cultivar of *Sanvitalia* plant, botanically known as *Sanvitalia speciosa*, of the Asteraceae family, commonly referred to as the creeping zinnia, and hereinafter referred to by the variety denomination 'DANVITAL4'.

The new *Sanvitalia speciosa* 'DANVITAL4' is a product of a planned breeding program conducted by the inventor, Gavriel Danziger, in Moshav Mishmar Hashiva, Israel. The objective of the breeding program was to develop a new *Sanvitalia* cultivar with compact, branched growth habit and abundant flowering.

The new *Sanvitalia speciosa* 'DANVITAL4' originated from open pollination by an unknown *Sanvitalia speciosa* of the unpatented, female, seed parent, *Sanvitalia speciosa* designated cv. 07-126, in a controlled breeding program by the inventor, Gavriel Danziger, in 2008 in Moshav Mishmar Hashiva, Israel. The new *Sanvitalia speciosa* 'DANVITAL4' was discovered and selected by the inventor, Gavriel Danziger, as a single flowering plant within the progeny of the stated cross in a controlled environment in July 2008 in Moshav Mishmar Hashiva, Israel.

Asexual reproduction of the new *Sanvitalia speciosa* 'DANVITAL4' by vegetative tip cuttings was first performed in August 2008 in Moshav Mishmar Hashiva, Israel, and has demonstrated that the combination of characteristics as herein disclosed for the new cultivar are firmly fixed and retained through successive generations of asexual reproduction. The new cultivar reproduces true-to-type.

BRIEF SUMMARY OF THE INVENTION

The following traits have been repeatedly observed and are determined to be unique characteristics of 'DANVITAL4', which in combination distinguish this *Sanvitalia speciosa* as a new and distinct cultivar:

1. mounding and trailing plant habit;
2. compact growth habit with good branching;
3. about 200 inflorescences per plant, consisting of ray florets that are primarily yellow in color and disc florets that are primarily green in color; and
4. medium tolerance to heat.

Plants of the new *Sanvitalia speciosa* 'DANVITAL4' differ from plants of the female parent, *Sanvitalia speciosa* designated cv. 07-126 (unpatented), in the characteristics described in Table 1.

TABLE 1

| Characteristic | New Cultivar 'DANVITAL4' | Female Parent cv.07-126 unpatented |
|---|---|---|
| Size: | | |
| Height | About 10 cm | About 6 cm |
| Diameter | About 30 cm | About 25 cm |
| Overall Plant Shape | Mounded and trailing | Trailing |
| Quantity of Leaves per Lateral Branch | About 10 to 15 | About 15 to 20 |
| Leaf Average Size | | |
| Length | About 2.5 cm | About 3 cm |
| Width | About 1.5 cm | About 2 cm |
| Quantity of Inflorescences per Plant | About 200 buds and open inflorescences | About 150 buds and open inflorescences |
| Inflorescence Size | | |
| Diameter | About 1.8 cm | About 1.2 cm |
| Depth | About 0.5 cm | About 0.5 cm |

TABLE 1-continued

| Characteristic | New Cultivar 'DANVITAL4' | Female Parent cv.07-126 unpatented |
|---|---|---|
| Floret Color (when fully opened) | Ray: Yellow, RHS 9A Disc: Primarily, Yellow-green, RHS 151A, with Yellow-green, RHS 151B, at apex, and Yellow-green, RHS 150D, at margin | Ray: Yellow, RHS 5B Disc: Yellow-green, RHS 154B |

Of the many commercial cultivars known to the present inventor, the most similar in comparison to the new *Sanvitalia speciosa* 'DANVITAL4' is the *Sanvitalia speciosa* 'SUPERBINI' (patented, EU-CPVO Plant Breeder's Right No. 18711). Plants of 'DANVITA4' differ from plants of 'SUPERBINI' in the characteristics described in Table 2.

TABLE 2

| Characteristic | New Cultivar 'DANVITAL4' | Comparison Cultivar 'SUPERBINI' patented |
|---|---|---|
| Size: | | |
| Height | About 10 cm | About 13 cm |
| Diameter | About 30 cm | About 35 cm |
| Overall Plant Shape | Mounded and trailing | Rounded |
| Quantity of Leaves per Lateral Branch | About 10 to 15 | About 15 to 20 |
| Leaf Average Size | | |
| Length | About 2.5 cm | About 4.0 cm |
| Width | About 1.5 cm | About 1.8 cm |
| Quantity of Inflorescences per Plant | About 200 buds and open infloresecences | About 150 buds and open infloresecences |
| Inflorescence Size | | |
| Diameter | About 1.8 cm | About 2.0 cm |
| Depth | About 0.5 cm | About 0.6 cm |
| Floret Color (when fully opened) | Ray: Yellow, RHS 9A Disc: Primarily, Yellow-green, RHS 151A, with Yellow-green, RHS 151B, at apex, and Yellow-green, RHS 150D, at margin | Ray: Yellow, RHS 12A Disc: Green, RHS 143C |

BRIEF DESCRIPTION OF THE PHOTOGRAPHS

The accompanying photographs illustrate the overall appearance of the new *Sanvitalia* 'DANVITAL4' showing the colors as true as is reasonably possible with colored reproductions of this type. Colors in the photographs may differ slightly from the color value cited in the detailed botanical description which accurately describe the color of 'DANVITAL4'.

DETAILED BOTANICAL DESCRIPTION

Figure 1:
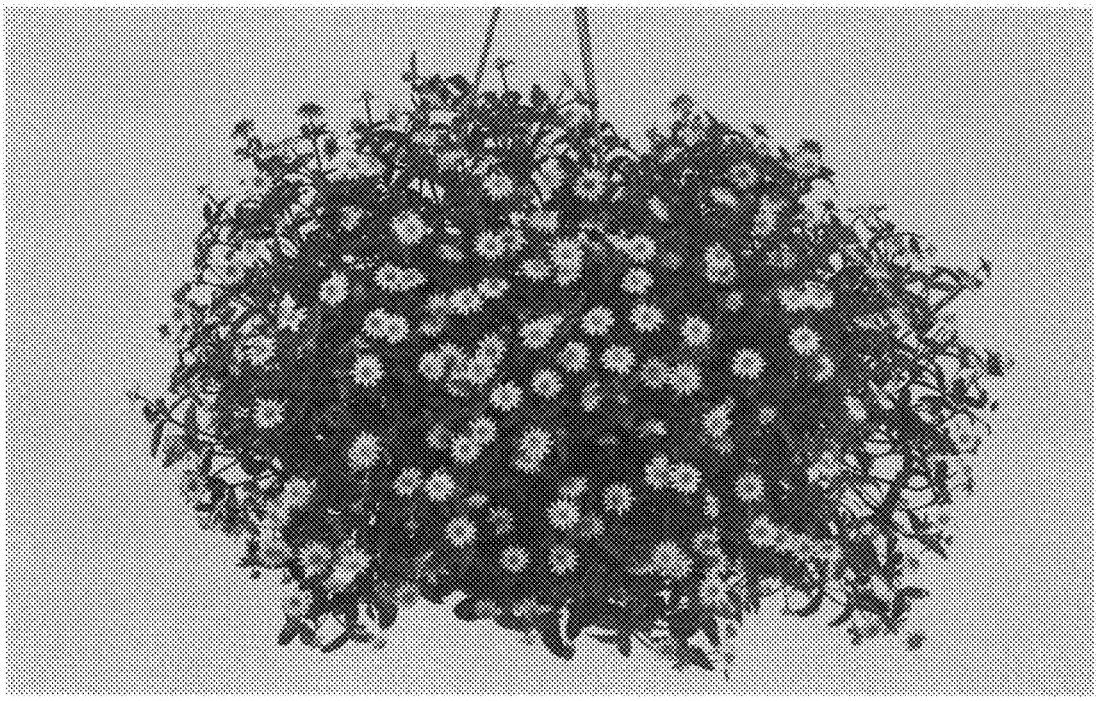
FIG. 1 shows a side view perspective a typical flowering plant of 'DANVITAL4' in a hanging planter, at 3 months of age after planting.
Figure 2:
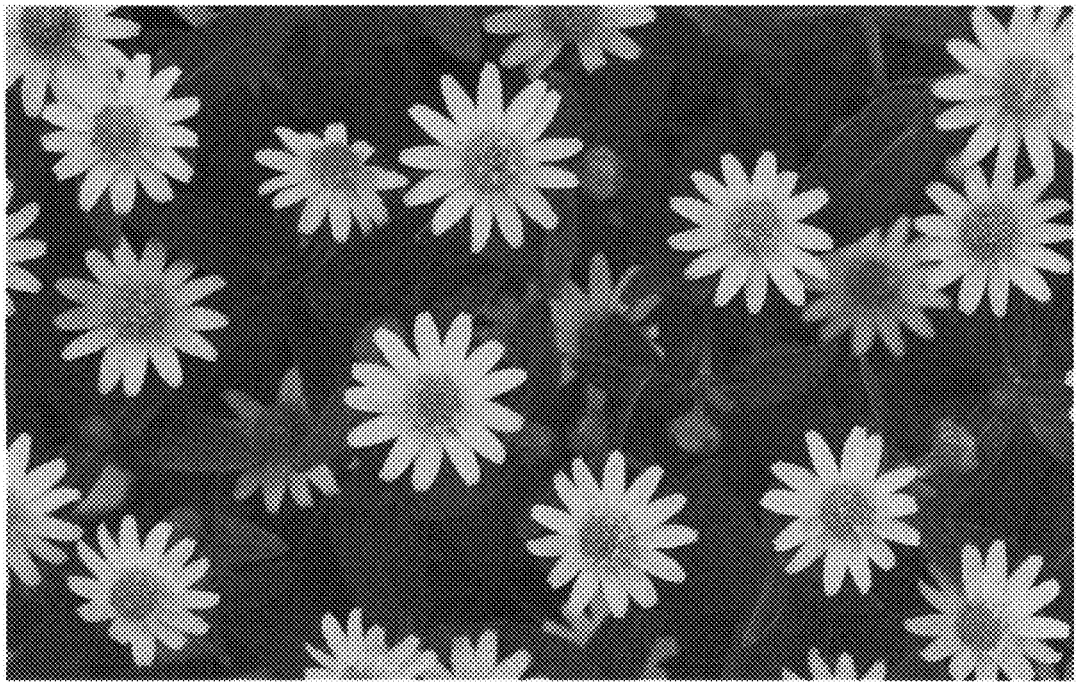
FIG. 2 shows a close-up view of the typical flowers, buds and leaves of 'DANVITAL4' at 3 months of age after planting.

The new *Sanvitalia* 'DANVITAL4' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Sanvitalia* 'DANVITAL4' as grown in a greenhouse in Moshav Mishmar Hashiva, Israel, under conditions which closely approximate those generally used in commercial practice.

The 'DANVITAL4' plants described herein were grown in 13 cm pots in a greenhouse in Moshav Mishmar Hashiva, Israel, with the day temperatures ranging from 22° C. to 25° C. and night temperatures ranging from 15° C. to 18° C. Plants of 'DANVITAL4' were fertilized up to a level of 150 ppm N, 70 ppm P and 150 ppm K.

Color references are made to The Royal Horticultural Society Colour Chart (R.H.S.), 2001 Edition, except where general colors of ordinary significance are used. Color values were taken under daylight conditions at approximately noon in Moshav Mishmar Hashiva, Israel. The age of the 'DANVITAL4' plants described is about 12 weeks.

Classification:

*Botanical.*—*Sanvitalia speciosa.*

Parentage:

*Female or seed parent.*—*Sanvitalia speciosa* designated cv. 07-126 (unpatented).

*Male or pollen parent.*—Open pollination by an unknown *Sanvitalia speciosa* cultivar.

Propagation:

*Type.*—Vegetative tip cuttings.

*Time and temperature to initiate roots.*—Summer: About 7 to 9 days at 18° C. to 22° C. in tunnels in a greenhouse. Winter: About 10 to 14 days at 15° C. to 18° C. in tunnels in a greenhouse.

*Time and temperature to develop roots.*—Summer: About 14 to 16 days at 18° C. to 22° C. in tunnels in a greenhouse. Winter: About 17 to 21 days at 15° C. to 18° C. in tunnels in a greenhouse.

*Rooting description.*—100% rooting.

*Rooting habit.*—Fine, fibrous and branching.

Plant description:

*General appearance and form.*—Mounding and trailing.

*Growth and branching habit.*—Freely branching with lateral flowering branches forming at every node; dense and bushy.

*Growth rate/vigor.*—Medium.

*Plant height (soil level to top of plant plane).*—About 10 cm.

*Plant spread.*—About 30 cm.

*Crop time to produce a mature flowering plant.*—After rooting, about 12 weeks are required to produce finished flowering plants in 13 cm pots.

Branches:

*Number of branches per plant.*—About 6 primary; about 20 secondary.

*Length.*—Primary: About 15 cm. Secondary: About 8 cm (including flowers).

*Diameter.*—About 0.2 cm.

*Internode length.*—About 2 cm.

*Strength.*—Medium.

*Apect.*—Initally upright, then bending outwardly.

*Texture.*—Glabrous.

*Color.*—Upper surface: Yellow-Green, RHS 145B. Lower surface: Yellow-Green, RHS 145B.

Foliage description:

*Arrangement*.—Opposite, simple, sessile.

*Length*.—About 2.5 cm.

*Width*.—About 1.5 cm.

*Overall shape of leaf*.—Elliptic.

*Shape at apex*.—Acute.

*Shape at base*.—Obtuse.

*Margin*.—Entire.

*Texture*.—Upper surface: Slightly pubescent. Lower surface: Slightly pubescent.

*Color of developing foliage*.—Upper surface: Green, RHS 137A. Lower surface: Green, RHS 137B.

*Color of mature foliage*.—Upper surface: Green, RHS 137A. Under surface: Green, RHS 137C.

*Venation pattern*.—Pinnate.

*Venation color*.—Upper surface: Yellow-Green, RHS 144 B. Under surface: Yellow-Green, RHS 144 B.

Inflorescence description:

*Appearance*.—Terminal and axillary inflorescences held above and beyond the foliage. Daisy inflorescence form, with oblong-shaped ray florets and disc florets massed at the center; ray and disc florets arranged acropetally on a capitulum. Inflorescences face upright or outward.

*Natural flowering season*.—Continuous throughout the spring and summer in temperate regions.

*Time to flower*.—About 30 to 40 days after planting (longevity of individual inflorescences is dependent on temperature and light conditions).

*Postproduction longevity*.—Inflorescences maintain good color and substance for about 14 days on the plant when grown in an outdoor environment. Inflorescences not persistent.

*Quantity of inflorescences*.—Freely flowering; about 200 buds and open inflorescences per plant.

*Fragrance*.—None.

*Bud*.—Rate of opening (from showing color to fully open inflorescence): About 3 to 4 days. Length: About 0.5 cm. Diameter: About 0.8 cm. Shape: Rounded. Texture: Slightly velvety. Color: Yellow-green, RHS 154A.

*Peduncle*.—Length: About 0.9 cm to 1.1 cm. Diameter: About 1 mm. Appearance and angle: About 45° from vertical. Strength: Medium. Texture: Slightly velvety. Color: Yellow-Green, RHS 144B.

*Inflorescence*.—Inflorescence depth (height): About 0.5 cm. Inflorescence diameter About 1.8 cm. Disc diameter: About 0.6 cm. Receptacle diameter: About 8 mm. Receptable height: About 2 mm. Receptacle shape: Conical. Receptacle color: Green, RHS 137B.

*Ray florets*.—Arrangement: About 1 whorl of ray florets, each with about 12 to 13 florets to equal a total of about 13 ray florets per capitulum (depending on light and temperature conditions). Orientation: Initially 45° from vertical, with development, close to 90° from vertical. Length: About 6 mm. Width: About 2 mm. Overall shape: Oblong. Shape at apex: Obtuse. Shape at base: Fused into short corolla tube. Margin: Entire. Texture: Upper surface: Glabrous. Under surface: Glabrous. Color (when opening): Upper surface: Yellow-Green, RHS 144A, at apex, to Yellow, RHS 9A, at base and at margin. Under surface: Green, RHS 143B, at apex, to Yellow-green, RHS 154B, at base and Yellow-green, RHS 154A, at margin. Color (when fully opened): Upper surface: Yellow, RHS 9A, at apex, base and margin. Under surface: Green, RHS 143C, at apex, to Yellow-green, RHS 154C, at base, and Yellow-green, RHS 154 B, at margin.

*Disc florets*.—Arrangement: Massed at center of capitulum, in about 8 whorl(s) of disc florets, each with about 15 to 20 florets to equal a total of about 140 disc florets per capitulum. Length: About 1 mm. Width: At apex: About 0.2 mm. At base: About 0.5 mm. Disc area diameter: About 6 mm. Overall shape: Tubular, elongated. Shape at apex: Star with 5 triangular tips. Shape at base: Fused to tube. Margin: Entire. Texture: Upper surface: Glabrous; Under surface: Glabrous. Color (when opening): All surfaces: Primarily, Yellow-green, RHS 144A, with Yellow-green, RHS 144B, at apex, and Yellow-green, RHS 145C, at margin. Color (when fully opened): All surfaces: Primarily, Yellow-green, RHS 151A, with Yellow-green, RHS 151B, at apex, and Yellow-green, RHS 150D, at margin.

*Phyllaries*.—Quantity per inflorescence: About 5 in a single whorl, fused at base. Length: About 0.5 cm. Width: About 0.4 cm. Overall shape: Cordate. Apex shape: Acute. Base shape: Fused. Margin: Entire. Texture: Upper surface: Glabrous. Under surface: Glabrous. Color: Upper surface: Green, RHS 137B. Under surface: Green, RHS 137C.

Reproductive organs:

*Androecium* (*on disc florets only*).—Stamen number: 5 per floret; fused around style. Stamen length: About 2 mm. Anther shape: Ellipsoid. Anther length: About 1 mm. Anther color: Yellow, RHS 3A. Pollen amount: Moderate. Pollen color: Yellow, RHS 3A.

*Gynoecium* (*on ray and disc florets*).—Quantity: 1 per floret. Pistil length: About 2 mm. Stigma shape: Two-parted. Stigma length: About 1.5 mm. Stigma color: Yellow, RHS 6A. Style length: About 0.5 mm. Style color: Yellow, RHS 2D. Ovary diameter: About 1 mm. Ovary color: Yellow-green, RHS 147C.

Seed:

*Quantity per inflorescence*.—About 13.

*Shape*.—Oblate.

*Length*.—About 1.5 mm.

*Diameter*.—About 1.0 mm.

*Texture*.—Glabrous.

*Color*.—Grey-Brown, RHS 199A.

Fruit: Achene, Grey-Brown, RHS 199B, approximately 0.3 cm.

Disease/pest resistance: Plants of the new *Sanvitalia* have shown good resistance to pathogens and pests.

Disease/pest susceptibility: Plants of the new *Sanvitalia* have shown low susceptibility to pathogens and pests.

Temperature tolerance: Plants of the new *Sanvitalia* have exhibited good tolerance to rain, wind and temperatures from about +15° C. to about +25° C.

What is claimed is:

1. A new and distinct cultivar of *Sanvitalia speciosa* plant named 'DANVITAL4', as illustrated and described herein.

* * * * *